US008206762B2

(12) United States Patent
Freund et al.

(10) Patent No.: US 8,206,762 B2
(45) Date of Patent: Jun. 26, 2012

(54) **USE OF *ECHINACEA* OR PREPARATIONS THEREOF IN COMPOSITIONS FOR THE TREATMENT OF ANXIETY**

(76) Inventors: Tamás Freund, Budapest (HU); József Haller, Budapest (HU)

(*) Notice: Subject to any disclaimer, the term of this patent is extended or adjusted under 35 U.S.C. 154(b) by 248 days.

(21) Appl. No.: 12/304,558

(22) PCT Filed: Jun. 13, 2007

(86) PCT No.: PCT/HU2007/000052
§ 371 (c)(1),
(2), (4) Date: Feb. 10, 2009

(87) PCT Pub. No.: WO2007/144676
PCT Pub. Date: Dec. 21, 2007

(65) Prior Publication Data
US 2009/0285907 A1 Nov. 19, 2009

(30) Foreign Application Priority Data
Jun. 13, 2006 (HU) .................................. 0600489

(51) Int. Cl.
*A61K 36/28* (2006.01)
(52) U.S. Cl. ........................................................ 424/737
(58) Field of Classification Search .................. None
See application file for complete search history.

(56) References Cited

U.S. PATENT DOCUMENTS
6,238,696 B1 * 5/2001 Wang .............................. 424/452
2003/0152652 A1 * 8/2003 Baker et al. ................... 424/737

FOREIGN PATENT DOCUMENTS
RU 2241486 C1 12/2004

OTHER PUBLICATIONS

Cognitive Therapy and Research, vol. 26, No. 1, Feb. 2002, pp. 39-55, "Vulnerability to social stress: coping as a Mediator or Moderator of Sociotropy and Symptoms of Anxiety and Depression".*
How Stress, Anxiety, and Depression Affect Your Health the website: http://www.webmd.com/depression/stress-anxiety-depression.*
Shah et al., Evaluation of *Echinacea* for the prevention and treatment of the common cold: a meta-analysis, Lancet Infect Dis, Jul. 2007, vol. 7, pp. 473-480.
Perri et al., Safety and Efficacy of *Echinacea* (*Echinacea angustifolia, E. purpurea* and *E. pallida*) During Pregnancy and Lactation, Can J Clin Pharmacol, Nov. 2006, vol. 13, pp. e262-e267.
Woelkart, K. et al., The Endocannabinoid System as a Target for Alkamides from *Echinacea angustifolia* Roots, Planta Med, 2005; vol. 71, pp. 701-705.
Pacher et al., The Endocannibinoid System as an Emerging Target of Pharmacotherapy, Pharmacol Rev, 2006, vol. 58, pp. 389-462.
Fabre and McLendon, The Efficacy and Safety of Nabilone (A Synthetic Cannabinoid) in the Treatment of Anxiety, J Clin Pharmacol, 1981; vol. 21 Suppl, pp. 377S-382S.
Fusar-Poli et al., Distinct Effects of delta9-Tetrahydrocannabinol and Cannabidiol on Neural Activation During Emotional Processing, Arch Gen Psychiatry, Jan. 2009, vol. 66, pp. 95-105.
Patel and Hillard, Pharmacological Evaluation of Cannabinoid Receptor Ligands in a Mouse Model of Anxiety: Further Evidence for an Anxiolytic Role for Endogenous Cannabinoid Signaling, J Pharmacol Exp Ther., 2006; vol. 318, pp. 304-311.
Arevalo et al., Cannabinoid effects on anxiety-related behaviours and hypothalamic neurotransmitters, Pharmacol Biochem Behav, 2001, vol. 70, pp. 123-131.
Genn et al., Unconditioned and conditioned anxiogenic effects of the cannabinoid receptor agonist CP 55,940 in the social interaction test, Pharmacol Biochem Behav, 2004, vol. 77, pp. 567-573.
Whiting, GABA-A receptors: a viable target for novel anxiolytics?, Current Opinion in Pharmacology, 2006; vol. 6, pp. 24-29.
Gaetani et al., Anandamide hydrolysis: a new target for anti-anxiety drugs?, Trends in Molecular Medicine, Nov. 2003, vol. 9, pp. 474-478.
Haller et al.: "The Effect of *Echinacea* Preparations in Three Laboratory Tests of Anxiety: Comparison with Chlordiazeposxide", Phytotherapy Research, 2010, vol. 24, pp. 1605-1613.
Selye: "A Syndrome produced by Diverse Nocuous Agents", Nature, 1936, p. 32.
Cameron et al.: "Systemic Hormonal and Physiological Abnormalities in Anxiety Disorders", Psychoneuroendocrinology, 1988, vol. 13, No. 4, pp. 287-307.
Roth et al.: "Stress, Behavioral Arousal, and Open Field Acitivity—A Reexamination of Emotionality in the Rat", Neuroscience & Biobehavioral Reviews, 1979, vol. 3, pp. 247-263.
Korte et al.: "The Darwinian concept of stress: benefits of allostasis and costs of allostatic load and the trade-offs in health and disease", Neuroscience and Biobehavioral Reviews, 2005, vol. 29, pp. 3-38.
McEwen: "Physiology and Neurobiology of Stress and Adaptation: Central Role of the Brain", Pysiol. Rev., 2007, vol. 87, pp. 873-904.

* cited by examiner

*Primary Examiner* — Christopher R. Tate
*Assistant Examiner* — Deborah A. Davis
(74) *Attorney, Agent, or Firm* — Jason D. Voight

(57) ABSTRACT

The present invention relates to the use of *Echinacea* or *Echinacea* preparations for the manufacture of pharmaceutical compositions which can be used to relieve natural occurrences of anxiety. The compositions can also be used to relieve the symptoms of various anxiety disorders including generalized anxiety, panic, acute traumatic stress disorder, post-traumatic stress disorder, phobias of various kinds including social phobia, compulsive disorders, and anxiety states related to withdrawal from drugs (e.g. alcohol, tobacco, and illicit drugs). The phrase "*Echinacea*" embraces *Echinacea purpurea, Echinacea angustifolia, Echinacea pallida*, or their combination. *Echinacea* preparations can be administered alone, but should preferably be used in combination with a vitamin mix (including but not limited to B1, B2, niacin, pantothenic acid, B6, biotin, folic acid B12, and/or C vitamin) and/or a mineral mix (including but not limited to calcium, magnesium and zinc).

8 Claims, 3 Drawing Sheets

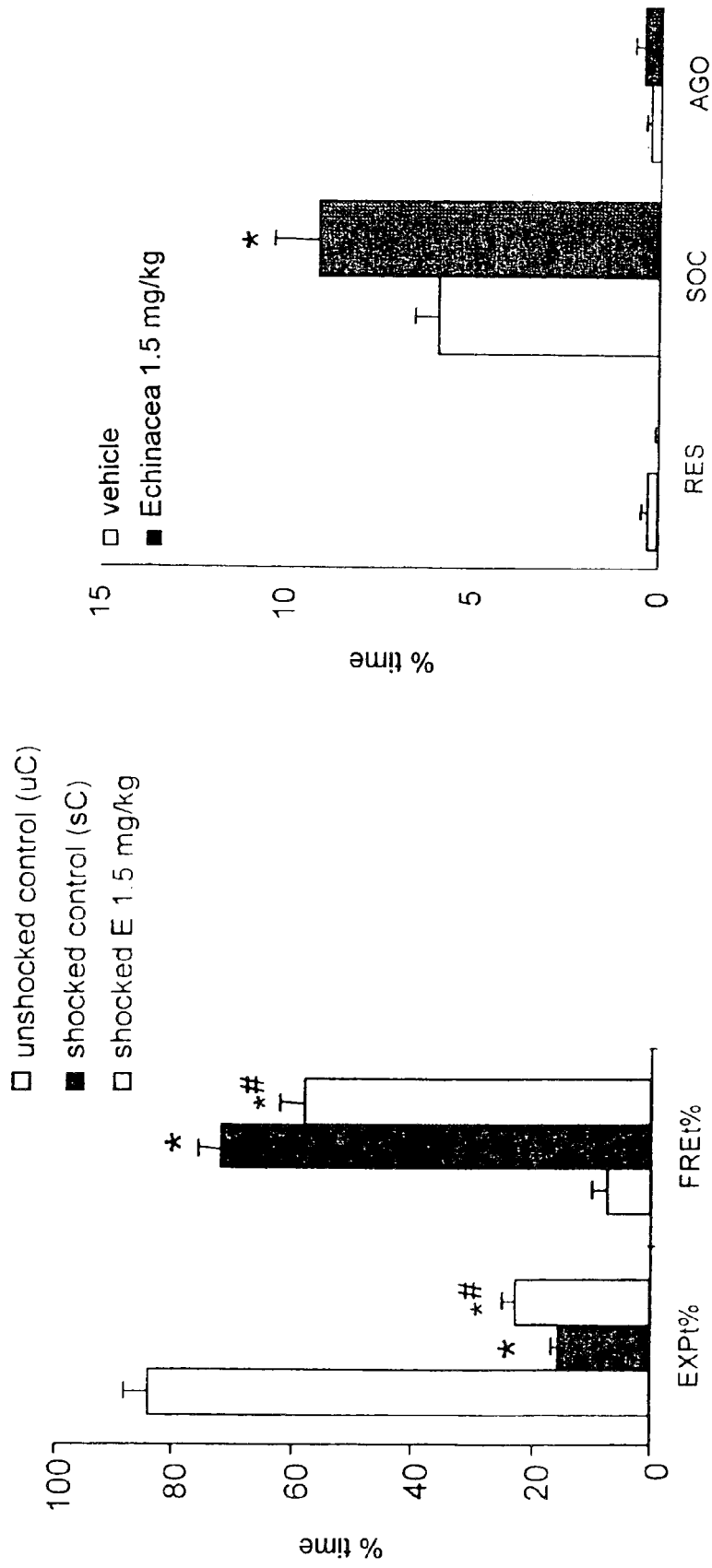

USE OF *ECHINACEA* OR PREPARATIONS THEREOF IN COMPOSITIONS FOR THE TREATMENT OF ANXIETY

This is the National Stage of International Application PCT/HU2007/000052, filed Jun. 13, 2007.

The present invention relates to the use of *Echinacea* and preparations made thereof for the treatment of anxiety and to the use of them for the manufacture of the corresponding pharmaceutical compositions.

TECHNICAL BACKGROUND

1. Medicinal Uses of *Echinacea* Species

There are three *Echinacea* species (*E. purpurea, E. angustifolia*, and *E. pallida*), which were used first by Native Americans for a variety of ailments, including pain relief and wound treatment, mouth sores, as an antidote against various poisons, and for symptoms associated with the common cold (Borchers et al., 2000; Huntley et al., 2005). *Echinacea* preparations have since become one of the most popular medicinal botanicals in Europe and the United States.

1.1. Contemporary Indications

The PubMed Medline electronic database comprises 420 records (346 with abstracts) that contain the word "*Echinacea*" in their title or abstract. The interest in this plant increased considerably over the past 25 years (FIG. 1.).

For the subject areas covered see Table 1.

TABLE 1

Subject areas covered by publications on *Echinacea*

| Subject area | % of all papers |
| --- | --- |
| Immunity | 21.7 |
| Technical details of use* | 13.3 |
| Popularity as a phytomedical agent | 13.0 |
| Safety | 13.0 |
| Effects on cold and respiratory infections | 10.5 |
| Active ingredients | 9.0 |
| General presentation of medical uses | 4.8 |
| Effects on enzyme activities† | 3.6 |
| Virus infections other than respiratory | 2.1 |
| Antioxidant | 1.8 |
| Sexual functions | 1.2 |
| Antimutagenic effects/cancer | 0.9 |
| Radioprotection | 0.3 |
| Antifugal activity | 0.3 |
| Wound healing | 0.3 |
| Hepatoprotection | 0.3 |
| Other (mainly plant science work) | 3.6 |

*production process, stability, absorption, pharmacokynetics, etc;
†mainly enzymes involved in drug absorption and degradation Due to their immunostimulant, antimicrobial and antiviral effects, *Echinacea* preparations are recommended for the prevention and treatment of common cold and other respiratory infections, inflammations and some non cold-related viral infections (Borchers et al., 2000; Currier and Miller, 2000; Linde et al., 2006; Melchart et al. 1998; Percival, 2000; Perfect et al., 2005; Randolph et al., 2003). Some evidence suggests that *Echinacea* preparations can be used for the treatment of tumors and wounds, and possess antioxidant, radioprotective, and hepatoprotective effects (Mishima et al., 2004; Rusu et al., 2005; Speroni et al., 2000; Zink and Chaffin, 1998).

No *Echinacea* preparation was shown to affect anxiety or anxiety-related behaviors, and none of the preparations was indicated for the treatment of anxiety disorders.

1.2. Preparations and Active Ingredients

The known active ingredients of *Echinacea* preparations are polysaccharides, glycoproteins, caffeic acid derivatives and alkamides (Bauer, 1996; Schulz et al., 2002; Wu et al., 2004; Luo et al., 2003; Thude et al., 2005). They also contain trace elements e.g. Fe, Cu, Mn, Li, Ca, Mg, Zn, and Ni (Razic et al., 2003). Both roots and aerial parts of *Echinacea* plants are being used as dried (occasionally powdered) plant parts, aqueous and hydro-alcoholic extracts. Hydro-alcoholic extracts are the most rich in active constituents, although saccharine content may decrease with increasing the concentration of alcohol during extraction (Wack and Blaschek, 2006).

1.3. Mechanisms of Action

Recently, the immunostimulant effects of *Echinacea* extracts was linked to the cannabinoid $CB_2$ receptor agonist activity of certain alkamides contained by the plant (Woelkart et al., 2005; Raduner et al., 2006). The cannabinoid $CB_2$ receptors are located peripherally on cells involved in the immune response, and their role in controlling immune functions is well known (Munro et al., 1993; Piomelli, 2003). Beyond affecting the $CB_2$ receptor, certain *Echinacea* alkamides were shown to bind to the cannabinoid $CB_1$ receptor, which is located in the central nervous system, and affects emotionality (Matsuda et al., 1993; Piomelli, 2003). Binding appears weak (one order of magnitude weaker than binding to the $CB_2$ receptor), but is not negligible.

1.4. The Relevance of the Newly Discovered Mechanisms of Action for Anxiety

The involvement of cannabinoids [i.e. compounds binding to cannabinoid $CB_1$ and/or $CB_2$ receptor(s)] in anxiety is controversial; therefore, the effects of *Echinacea* extracts on anxiety could not be forecasted. $CB_1$ agonists increased anxiety in rats, the subjects of the studies reported here (Arevalo et al. 2001; Genn et al., 2004; Giuliani et al., 2000; Hill and Gorzalka; 2004; Marco et al., 2004; Marin et al., 2003; McLaughlin et al., 2005; Rodriguez de Fonseca et al., 1996). Surprisingly, the cannabinoid antagonist SR-141716A was also anxiogenic in rats (Navarro et al., 1997). Data reported in mice are similarly contradictory, as the genetic disruption of the CB1 receptor was anxiogenic, whereas its pharmacological blockade by the antagonist SR-141716A was anxiolytic (Berrendero and Maldonado, 2002; Griebel et al., 2005; Haller et al., 2002; 2004a; 2004b. Maccarrone et al., 2002; Martin et al., 2002; Rodgers et al., 2003; Rodgers et al., 2005; Uriguen et at, 2004; Valjent et al., 2002). AM-251, another antagonist was anxiogenic. Data in humans are not less confusing. While some studies suggest that cannabinoids may be used to relieve anxiety (Fabre and McLendon, 1981; Sethi et al., 1986), other studies list anxiety among the main consequences of cannabinoid consumption (Tunving, 1987; Croxford, 2003).

SUMMARY OF THE INVENTION

During our experiments we found that *Echinacea* preparations can be applied with success in the treatment of anxiety.

Accordingly, the present invention relates to the use of *Echinacea* or preparations made thereof for the manufacture of pharmaceutical compositions for the treatment of anxiety.

Further, the invention relates to pharmaceutical compositions for the treatment of anxiety containing as active ingredient *Echinacea* or preparations made thereof together with one or more pharmaceutically acceptable auxiliary/auxiliaries.

According to a preferred embodiment of the invention the pharmaceutical composition is in a liquid or solid dosage unit form, preferably manufactured for oral administration.

No known mechanisms of action of *Echinacea* extracts could forecast their surprisingly strong anxiolytic effects, moreover, surprisingly, this effect can be observed when the *Echinacea* extract is applied at doses considerably lower than those used for traditional indications. The plant is among the most widely used complementary/alternative medicines worldwide, and is well tolerated. The test data shown below present evidence for the potential of this plant for the alternative treatment of various natural (not disorder-like) anxiety states, and to relieve the symptoms of various anxiety disorders.

DETAILED DESCRIPTION OF THE INVENTION

The invention relates to the use of *Echinacea* or *Echinacea* preparations for the manufacture of pharmaceutical compositions which can be used to relieve natural occurrences of anxiety as well as symptoms of anxiety disorders. Examples of natural (non disorder-like) anxiety states include but are not limited to anxious feelings induced by dental treatment (or the anticipation of such treatment), academic or other examinations, the contracting of serious diseases, court appearances, business meetings or public speaking. The compositions of the present invention can also be used to relieve the symptoms of various anxiety states including generalized anxiety, panic, acute traumatic stress disorder, post-traumatic stress disorder, phobias of various kinds including social phobia, compulsive disorders, and anxiety states related to withdrawal from drugs (e.g. alcohol, tobacco, and illicit drugs). The compositions of the present invention may also be used to easy withdrawal from conventional anxiolytic medication, and to prevent relapse after such treatments.

The form and dosage of *Echinacea*-based pharmaceutical compositions and the relating treatments are described below. The plant can be administered alone, but should preferably be used in combination with a vitamin and/or mineral mix as described below.

The phrase "*Echinacea*" embraces *Echinacea purpurea*, *Echinacea angustifolia*, *Echinacea pallida*, or their combination. Both roots and aerial parts of the plants—or their combination—can be used. The preferable plant parts are the roots. Preferably the *Echinacea* is cut or ground into small pieces or the dried *Echinacea* is powdered. Preferably, the *Echinacea* is *Echinacea purpurea*.

*Echinacea* preparations can be made from *Echinacea* or the above parts of the *Echinacea* by known methods, e.g. by digesting, macerating or extracting the natural *Echinacea* or the above parts of the *Echinacea*.

The pharmaceutical compositions according to the present invention (abbreviated as "composition") may contain natural pieces of *Echinacea* or *Echinacea* preparations or combination thereof.

The compositions may be administered to humans or animals by bronchial inhalations, intramuscularly, intravenously, nasally, orally, parenterally, subcutaneously, sublingually, or transdermally. The preferred route of administration is oral ingestion. The compositions may be administered in solid, semi-solid, or liquid forms.

Solid forms include, but are not limited to ground plants or parts of plant, ingested in its natural form, or as dried and/or powdered parts of plant.

Semi-solid forms include but are not limited to capsules, caplets, lozenges, powders, and tablets, and include hard, chewable, and non-chewable forms. Specific examples of semi-solid forms include soft capsules that contain the plant preparation in oil suspension, hard tablets impregnated with liquid preparation and dried, and food-like forms such as candies.

Suitable liquid forms include but are not limited to solutions, tinctures, syrups, emulsions, and suspensions. Specific examples of liquid forms include teas, and alcoholic/hydroalcoholic extracts, that are administered in the form of drops. Preferably, the preparation should be a hydro-alcoholic extract, where the concentration of alcohol should be 20-80%.

In a preferred embodiment of the invention the composition is a hydro-alcoholic extract, e.g. an ethyl alcoholic tincture, which preferably has a dry residue content of 0.1 to 15% w/w, more preferably 0.2 to 5% w/w, most preferably 0.5 to 1.5% w/w.

The compositions should be administered 1-5 times a day. Preferably, it should be administered once daily in the morning or twice daily in the morning and evening. A single dose should be between 2 mg and 200 mg depending on the form of the preparation. Specific examples include 2-40 drops of a hydro-alcoholic extract containing 0.1-15% w/w dry residue. More preferably, the dose should be 5-20 drops of hydroalcoholic extracts containing 0.2 to 5% w/w of dry residue (in general, the volume of 20 drops is 1 ml). The dosage of other preparation forms should be calculated from the doses presented above for the administration of the hydro-alcoholic extract.

Our data detailed below show that, suprisingly, when the *Echinacea* extract is applied at doses considerably lower than those used for traditional indications it can rapidly and effectively decrease anxiety in humans. It means that preferably 0.5 to 10 ml, more preferably 1 to 5 ml, e.g. 2 ml per day from the tincture having a dry residue content of 0.5 to 1% w/w, e.g. 0.75% w/w from the said preferred ethyl alcoholic tincture causes an effective decrease in anxiety.

The addition of vitamins is based on the documented positive effect of vitamins on mood (Benton et al., 1995). Vitamin supplementation should be viewed as an adjuvant. The vitamin mix to be incorporated in the preparation includes but is not limited to B1 (5-25 mg), B2 (5-25 mg), niacin (5-70 mg), pantothenic acid (5-25 mg), B6 (5-15 mg), biotin (50-150 µg), folic acid (50-400 µg), B12 (5-10 µg), and/or C (30-500 mg) vitamin.

The addition of the mineral mix is based on the documented positive effect of minerals (especially in combination with vitamins) on mood (Carroll et al, 2000). Mineral supplementation should be considered an adjuvant. The mineral mix to be incorporated in the preparation includes but is not limited to calcium (10-100 mg), magnesium (10-100 mg), and zinc (1-10 mg).

The pharmaceutical composition according to the present invention may contain one or more food and/or pharmaceutical auxiliary/auxiliaries (e.g. processing aids, carriers, surface-active agents, colorants, sweeteners, solvents, disintegrators, coating materials) that dissolve or keep the components together, ensure appropriate absorption, or ensure a controlled release of active ingredients. Such formulations include liposome encapsulation, transdermal patches, formulations based on polyvinyl pyrrolidone, biodegradable polymers and alike. Examples of other auxiliaries include but are not limited to alcohol, aqueous dextrose, buffers, gelatins, glycols, gums, lipids, methylcellulose, natural fibers, proteins, starch, silica gel, various oils, water, water-soluble polymers, etc. These are examples not limitations.

The use of sweeteners of any kind may also be preferable especially in the case of food-like forms of administration.

DESCRIPTION OF THE FIGURES

FIG. 3 shows the effects of *Echinacea* in the conditioned fear test. The duration of exploration is expressed as % time (EXPt %) and the increased freezing is expressed as % time (FREt %). Meanings of further signs:
*Significant difference compared with uC.
*# Significant difference compared with sC.

FIG. 4 shows the effect of the *Echinacea* extract in the social interaction test of anxiety. Meanings of the signs RES: resting; SOC: social interactions, AGO: agonistic interactions.

EXAMPLE

Figure 1:
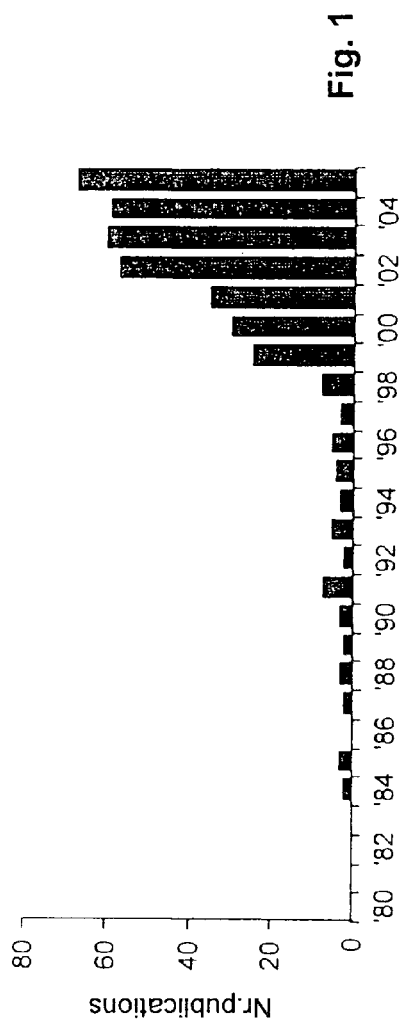
FIG. 1 shows publications containing the word *Echinacea* as covered by the electronic database PubMed Medline.

We conducted a series of preclinical studies to assess the potential of *Echinacea* preparations in the treatment of anxiety, and concluded that hydro-alcoholic *Echinacea* preparations decrease anxiety at doses that are lower than those applied for traditional uses.

We also conducted a preliminary human study to investigate the relevance of laboratory findings to humans. The State-Trait Anxiety Inventory was used to assess anxiety levels. Our findings demonstrate that hydro-alcoholic *Echinacea* preparations decrease anxiety at doses that are lower than those applied for traditional uses.

General Remarks
1. The Extract Used

For laboratory studies, we used an ethyl alcoholic *Echinacea purpurea* root tincture prepared by FitoChem Ltd. (H-2200 Monor, 14 Kossuth Str, ww.fitochem.hu), on the 21st of February, 2006 (Lot number FECH-010011205; analytical ID: 052/06). The dry residue was 1.7% w/w, whereas the lead content was less than 10 μg/g. Microbiological analysis provided satisfactory results (e.g. the total plate count was less than 1000 CFU/g). The extract containing 70% ethyl alcohol was stored at room temperature (validity date under these conditions: March, 2007), and used in experiments in April-May, 2006. Before use, ethyl alcohol was evaporated in vacuum at 4° C. by means of a Speed Vac Concentrator (Savant Instruments Inc., Farmingdale, USA). The residue was re-suspended in 0.4% methylcellulose (SIGMA Hungary, Budapest), and stored at −20° C. till use. The dose was expressed as mg dry residue/kg body weight. Treatments were administered 30 min before behavioral testing.

For human studies, we used a commercially available ethyl alcoholic *Echinacea purpurea* root tincture that is used as an immunostimulant for the common cold (Dr. Theiss *Echinacea* Drops, Dr. Theiss Naturwaren GmbH, Homburg, Germany, lot No. 01075, valid till 07.2009). The dry residue was 0.76% w/w. Before administration 20 drops (1 ml) of the tincture was dissolved in approximately 50-100 ml water. This dose of the tincture—considerably smaller than the one used for the treatment of common cold—contained 7.5 mg dry residue. Treatments were administered twice daily.

2. Experimental Subjects

The laboratory study was performed in Wistar rats provided by Charles-River Laboratories (Budapest, Hungary) that were maintained under a 12:12 h day:night schedule, with lights on at 0700 h. Rats had free access to standard rat chaw (Charles-River Laboratories, Budapest, Hungary), and tap water. Animal rooms were climatized. Temperature was held constant at 22±2° C., whereas relative humidity was 60±10%. Rats were kept in groups of five in macrolon cages measuring 45×35×30 cm. Their weight was around 200 g at the start of experiments.

The preliminary human study was performed in seven volunteers. For confidentiality reasons, they were selected from the entourage of the inventors. Their average age was 35.0±5.9 years (mean±SEM). Three participants were females whereas four were males. They were either students or intellectuals and were residents of Budapest, Hungary. All subjects belonged to middle/high income families. Three of them had diagnosed anxiety disorders, whereas the remaining 4 complained about work overload. They had no other psychiatric diagnoses. None of the subjects received pharmacological or psychological treatments in the 2 month that preceded the study and none were drug abusers. One of the subjects (a male) was a smoker.

3. Statistics

Data obtained in laboratory experiments were analyzed by Kruskall-Wallis ANOVA followed by Mann-Whitney post-hoc comparisons. Data were reported as mean±standard error of the mean (SEM). Plasma corticosterone data were evaluated by ANOVA.

The data obtained in the human study were analyzed by repeated measures ANOVA as time-related changes were important in this study. This analysis was followed by Fischer LSD post-hoc comparisons. Data were reported as mean±standard error of the mean (SEM).

Experiment 1
The Elevated Plus-Maze Test
a) General Disclosure

This test was described first by Pellow et al. (1984), and later became one of the most popular anxiety tests, frequently used for the identification of putative anxiolytics. It is based on the aversion shown by laboratory rodents towards open spaces. The apparatus consists of four arms, two of which are surrounded by walls (closed arms) whereas the other two are open. The level of anxiety correlates inversely with the exploration of the anxiogenic open arms (longer exploration of open arms indicates a decrease in anxiety). To avoid confounds with anxiety, the locomotor effects of compounds are evaluated based on closed arm entries (Hogg, 1996).

b) Detailed Description of the Applied Test Conditions

The elevated plus-maze (arm length 50 cm, arm width 17 cm; wall height 30 cm; platform height 80 cm) was made of dark grey painted wood, and lit by 4 white lamps of 40 W each (approximately 200 lx). 0.5 mm high ledges surrounded open arms. Rats were placed in the central area of the apparatus with head facing a closed arm. Exposure lasted 5 min. Closed arm entries are indicators of locomotor activity, whereas % time spent in open arms and % open arm entries are measures of anxiety. Behaviors were scored by experimenters blind to treatment conditions by means of a computer based event recorder.

c) Specific Details of the Tests Made

Two studies were run: Experiment 1A (Apr. 6-7, 2006) and 1B (Apr. 20-21, 2006). Experiment 1A studied the effects of 0 (vehicle), 0.5, 1, and 2 mg dry residue/kg body weight. The dose range studied in Experiment 1B was overlapping: 0 (vehicle), 1.5, 3, and 6 mg/kg *Echinacea*. Sample size was 10 animals per group.

Raw data, statistics and results are summarized and discussed below.

Experiment 2

Contextual Conditioned Fear a) General Disclosure

This test is the oldest anxiety test used in the laboratory, which was first described in early '50s (Brown et al., 1952). It is based on the anxiety-related behaviors shown by laboratory rodents when exposed to environments associated earlier with traumatic experiences. The main anxiety-related behavior in this test is "freezing" (i.e. no movement other than respiration) shown by rodents when re-exposed to the context associated earlier with shocks (Beck and Fibiger, 1995). In freezing rats, the exploration of the environment is naturally reduced.

b) Detailed Description of the Applied Test Conditions

Shocks were delivered and behavioral testing was performed in a separate, quiet room, with the experimenter leaving the room during testing. On the first day, rats were introduced into the Plexiglas shocking cage (30×30×30 cm). Shocks were administered via the grid floor of the box. Two shocks trains of 1 s were administered per min for 5 min (i.e. each rat received 10 shocks). Each shock train (100 V, 3 mA) was 1 s long and consisted of 0.01 s shocks separated by 0.02 s long breaks. Control mice were placed into a similar box for 5 mint but shocks were not delivered. 24 h later, mice were returned to the shock-box for 5 min. Shocks were not delivered. Behavior was recorded by a video camera, and later analyzed. The following variables were recorded, exploration (searching, sniffing movements directed towards the walls, grid or the air); grooming (grooming with fore paws and scratching with hind paws); resting (no locomotion, small postural changes allowed); freezing (no movements other than respiration); escape jumps (rapid jumps toward the wall with the intention to escape from the box). All three, the duration, frequency and latency of these behaviors were recorded. Behaviors were scored by experimenters blind to treatment conditions by means of a computer-based event recorder.

Plasma glucocorticoids were assessed in 200 µl blood sampled via tail incision on EDTA containing ice-cold tubes (Fluttert et al, 2000). This variant of the tail incision technique allows blood sampling without inducing changes in basal corticosterone levels. Blood was centrifuged at 4° C. and the plasma was kept at −20° C. until analyzed. Plasma corticosterone was measured by radioimmunoassay. The corticosterone antiserum was raised in rabbits against corticosterone-carboximethyloxime BSA. $^{125}$I-labelled corticosterone-carboximethyloxime-tyro sine-m ethyl ester was used as tracer. The interference with plasma transcortin was eliminated by inactivating transcortin at low pH. The sensitivity of the assay was 1 pmol/ml.

c) Specific Details of the Tests Made (26-27 April, 2006)

We tested the effects of the dose that showed the largest effects in the elevated plus-maze, namely the 1.5 mg/kg dose. On the first day, rats were treated with 0 (vehicle) or 1.5 mg/kg *Echinacea*. 30 min later rats were exposed to 10 electric shocks of 3 mA that were administered over 5 min as described above. Behavior was video recorded to assess whether drug treatment affected the immediate behavioral response to shock. After shock exposure, 0.05-0.1 ml blood was sampled for hormone measurements, and rats returned to their home cages. For hormone measurements, blood was sampled by tail incision (Fluttert et al., 2000), and plasma glucocorticoids were assessed by radioimmunoassay. One day later, rats were re-exposed to the shocking cages without receiving further shocks, and their behavior was assessed.

Raw data, statistics and results are summarized and discussed below.

Experiment 3

The Social Interaction Test a) General Disclosure

The social interaction test was first described by File and Hyde (1978), and today is frequently used for the laboratory testing of putative anxiolytics. The level of anxiety is evaluated in this test based on the behavior of subjects towards an unfamiliar rat met in an unfamiliar arena. Anxiolytics increase social interactions (File and Hyde 1978; Guy and Gardner, 1985).

b) Detailed Description of the Applied Test Conditions

The test arenas for the social interaction test were 6 cages measuring 60×40×50 (height) cm. Walls were made of opaque plastic except for the front wall which was transparent. Sawdust bedding was used, which was changed between sessions. Social encounters were evaluated in pairs of unfamiliar animals that had similar treatment. The following behaviors were recorded: resting (lying or standing; infrequent movements of the head or postural changes); locomotion/exploration (moving and/or sniffing movements directed towards the environment); self-care (grooming with forepaws and scratching with hind legs); social interaction and agonistic interactions. Social interactions included: sniffing directed towards the opponent; social grooming of the opponent; following the opponent who moves away (sniffing movements towards the back of the opponent associated). Agonistic interactions consisted of aggressive grooming (pushing down the opponent while he is standing, or trying to escape the situation; nibbling the fur and the skin with quick movements of the head; wrestling-like movements may be associated); lateral threat (pushing, approaching or moving around the opponent with arched back and piloerection); mutual upright (responding the upright of the opponent by upright and 'boxing' (pushing with the forepaws); this behavior may be associated with bite attempts or small jumps); chasing (following the fleeing opponent); biting attacks (biting the opponent while kicking and wrestling (clinch fights), or simple biting). Defensive behaviors (flight, defensive upright, immobility) and dominance related behaviors (dominant and submissive postures) were also recorded. Values were expressed as % time. Increased social interactions are consistent with an anxiolytic action.

c) Specific Details of the Tests Made

We tested the effects of the dose that showed the largest effects in the elevated plus-maze, namely the 1.5 mg/kg dose. Rats were treated with 0 (vehicle) or 1.5 mg/kg *Echinacea*. 30 min later rats were exposed to the social interaction test as described above.

Raw data, statistics and results are summarized and discussed below.

The Preliminary Human Study

The State-Trait Anxiety Inventory of Spielberger a) General Disclosure

The concepts of state and trait anxiety were elaborated by Spielberger (1966). Trait anxiety refers to relatively stable individual differences in anxiety proneness that is due to differences between people in the tendency to perceive stressful stimuli as dangerous or threatening and to respond to such situations with elevations in the intensity of their state anxiety. The State-Trait Anxiety Inventory for Adults and Children has been used extensively in research and clinical practice (Spielberger et al., 1983). It comprises separate selfreport scales for measuring state and trait anxiety. The State Anxiety Scale consists of twenty statements that evaluate how respondents feel "right now at this moment." The Trait Anxiety Scale consists of twenty statements that assess how people generally feel. We used in our studies the Hungarian version of the test (Perczel et al., 2005).

b) Detailed Description of the Applied Test Conditions

Subjects gave their informed consent to participation. All participants new about the extract; moreover, some used it earlier for the common indication. Each participant received a detailed protocol on the procedures to be applied. In principle, the treatment consisted of three phases: (1) A preliminary phase when baseline anxiety scores were recorded. (2) A treatment phase when subjects were treated with the *Echinacea* tincture as described below. (3) A follow-up phase, when treatments were stopped, but anxiety scores were recorded.

The dose was selected based on our laboratory findings and the doses used in rats for the stimulation of the immune system. As shown below, the *Echinacea* extract decreased anxiety in rats at doses that were several times lower than the ones that stimulate the immune system in the same species. Therefore, we applied in humans doses that were considerably lower than the ones used for the traditional indication. In humans, respiratory infections are treated with a startup dose of 50 drops (2.5 ml) followed by 10-20 drops (0.5-1 ml) every hour. Thus the dose that effectively stimulates the immune system in humans mounts up to 9-16 ml per day. To investigate effects on anxiety, we treated subjects with 2 ml extract per day.

c) Specific Details of the Tests Made

The baseline anxiety scores were evaluated twice in subjects, approximately 6 and 3 days before the application of the treatment. The treatment (20 drops i.e. 1 ml), was applied twice daily (in the morning and evening), except for one subject, who misunderstood the indications, and took only one treatment (in the morning). The length of the treatment was one week for 4 subjects, and three days for the remaining three subjects. Anxiety scores were recorded 1.5-2 h after the first treatment, and on the third day. In the subjects that received a one-week treatment, anxiety was also evaluated on the last (7th) day of the treatment, as well as 7 and 14 days after treatment cessation.

Raw Data of Experiment 1A

This experiment evaluated the effects of 0 (vehicle), 0.5, 1, and 2 mg dry residue of *Echinacea* per kg body weight in the elevated plus-maze test of anxiety.

Legend: vehicle, rats treated with vehicle; e05, rats treated with 0.5 mg/kg *Echinacea* extract; e1, rats treated with 1 mg/kg *Echinacea* extract; e2, rats treated with 2 mg/kg *Echinacea* extract. CLe, closed arm entries (measure of locomotor behavior); OPe, open arm entries (measure of anxiety); % OPe, % open arm entries (open arm entries/total arm entries*100; measure of anxiety); CL % t, time spent in closed arms (expressed as % of total time); CE % t, time spent in the central arena (expressed as % of total time); OP % t, time spent in open arms (expressed as % of total time).

| Group | CLe | OPe | % OPe | CL % t | CE % t | OP % t |
|---|---|---|---|---|---|---|
| vehicle | 11 | 8 | 42.11 | 73.60 | 12.60 | 13.20 |
| vehicle | 7 | 3 | 30.00 | 81.60 | 5.50 | 12.50 |
| vehicle | 4 | 2 | 33.33 | 79.70 | 8.50 | 11.50 |
| vehicle | 6 | 3 | 33.33 | 86.20 | 4.60 | 8.80 |
| vehicle | 9 | 4 | 30.77 | 76.20 | 11.50 | 11.70 |
| vehicle | 2 | 1 | 33.33 | 90.20 | 4.90 | 4.70 |
| vehicle | 5 | 2 | 28.57 | 83.70 | 12.60 | 3.40 |
| vehicle | 7 | 1 | 12.50 | 68.50 | 25.00 | 6.00 |
| vehicle | 9 | 2 | 18.18 | 72.90 | 22.10 | 4.50 |
| vehicle | 6 | 2 | 25.00 | 72.50 | 15.90 | 11.30 |
| e05 | 7 | 1 | 12.50 | 91.20 | 6.40 | 2.20 |
| e05 | 8 | 6 | 42.86 | 65.90 | 11.80 | 21.80 |
| e05 | 12 | 5 | 29.41 | 64.70 | 22.10 | 12.40 |
| e05 | 7 | 4 | 36.36 | 71.40 | 19.50 | 8.60 |
| e05 | 7 | 6 | 46.15 | 68.80 | 13.80 | 17.00 |
| e05 | 6 | 4 | 40.00 | 67.80 | 17.50 | 14.40 |
| e05 | 5 | 2 | 28.57 | 87.50 | 5.70 | 6.40 |
| e05 | 6 | 2 | 25.00 | 73.50 | 11.90 | 14.30 |
| e05 | 6 | 2 | 25.00 | 86.10 | 3.80 | 9.80 |
| e05 | 9 | 6 | 40.00 | 73.20 | 11.50 | 14.80 |
| e1 | 4 | 1 | 20.00 | 83.60 | 10.30 | 5.90 |
| e1 | 13 | 5 | 27.78 | 60.10 | 23.10 | 16.20 |
| e1 | 14 | 8 | 36.36 | 63.20 | 18.40 | 17.70 |
| e1 | 8 | 3 | 27.27 | 78.50 | 12.30 | 8.70 |
| e1 | 12 | 6 | 33.33 | 54.50 | 26.10 | 18.80 |
| e1 | 4 | 1 | 20.00 | 90.00 | 5.90 | 3.90 |
| e1 | 5 | 2 | 28.57 | 84.40 | 7.20 | 8.20 |
| e1 | 8 | 3 | 27.27 | 74.70 | 12.90 | 12.00 |
| e1 | 11 | 2 | 15.38 | 80.00 | 13.80 | 5.70 |
| e1 | 9 | 5 | 35.71 | 22.30 | 50.00 | 27.10 |
| e2 | 6 | 6 | 50.00 | 61.70 | 14.20 | 23.60 |
| e2 | 14 | 5 | 26.32 | 70.00 | 12.10 | 17.20 |
| e2 | 11 | 6 | 35.29 | 66.20 | 15.40 | 17.70 |
| e2 | 8 | 5 | 38.46 | 60.50 | 18.30 | 20.80 |
| e2 | 4 | 1 | 20.00 | 89.70 | 5.00 | 5.00 |
| e2 | 6 | 2 | 25.00 | 84.50 | 7.40 | 7.70 |
| e2 | 7 | 6 | 46.15 | 62.60 | 21.00 | 15.80 |
| e2 | 10 | 4 | 28.57 | 44.30 | 34.10 | 21.10 |
| e2 | 9 | 3 | 25.00 | 61.20 | 14.50 | 24.00 |
| e2 | 8 | 5 | 38.46 | 56.10 | 25.40 | 18.00 |

Raw Data of Experiment 1B

This experiment evaluated the effects of 0 (vehicle), 1.5, 3, and 6 mg dry residue of *Echinacea* per kg body weight in the elevated plus-maze test of anxiety.

Legend: vehicle, rats treated with vehicle; e1.5, rats treated with 1.5 mg/kg *Echinacea* extract; e3, rats treated with 3 mg/kg *Echinacea* extract; e6, rats treated with 6 mg/kg *Echinacea* extract; CLe, closed arm entries (measure of locomotor behavior); OPe, open arm entries (measure of anxiety); % OPe, % open arm entries (open arm entries/total arm entries*100; measure of anxiety); CL % t, time spent in closed arms (expressed as % of total time); CE % t, time spent in the central arena (expressed as % of total time); OP % t, time spent in open arms (expressed as % of total time).

| Group | CLe | OPe | % OPe | CL % t | CE % t | OP % t |
|---|---|---|---|---|---|---|
| vehicle | 4 | 1 | 20.0 | 82.5 | 9.4 | 7.8 |
| vehicle | 9 | 3 | 25.0 | 69.7 | 24.2 | 5.5 |
| vehicle | 5 | 2 | 28.6 | 88.2 | 7.3 | 4.1 |
| vehicle | 6 | 1 | 14.3 | 46.5 | 49.1 | 4.1 |
| vehicle | 10 | 8 | 44.4 | 55.8 | 17.7 | 25.9 |
| vehicle | 12 | 3 | 20.0 | 68.8 | 22.2 | 8.5 |
| vehicle | 6 | 3 | 33.3 | 75.4 | 20.5 | 3.7 |
| vehicle | 9 | 3 | 25.0 | 73.1 | 15.1 | 11.4 |
| vehicle | 10 | 8 | 44.4 | 51 | 22.7 | 25.6 |
| vehicle | 11 | 3 | 21.4 | 78.1 | 15 | 6.4 |
| e1.5 | 10 | 7 | 41.2 | 67.9 | 13.5 | 18.1 |
| e1.5 | 10 | 5 | 33.3 | 59.6 | 26 | 13.9 |
| e1.5 | 6 | 3 | 33.3 | 57 | 26.7 | 15.9 |
| e1.5 | 8 | 5 | 38.5 | 58.3 | 19.6 | 21.6 |
| e1.5 | 8 | 7 | 46.7 | 32.7 | 18.9 | 47.7 |
| e1.5 | 11 | 5 | 31.3 | 54.1 | 29.8 | 15.5 |
| e1.5 | 7 | 4 | 36.4 | 68.6 | 18 | 13 |
| e1.5 | 9 | 4 | 30.8 | 57.2 | 33.3 | 8.9 |
| e1.5 | 9 | 8 | 47.1 | 41.5 | 19.8 | 38.1 |
| e3 | 10 | 7 | 41.2 | 53.3 | 30.3 | 15.7 |

-continued

| Group | CLe | OPe | % OPe | CL % t | CE % t | OP % t |
|---|---|---|---|---|---|---|
| e3 | 11 | 7 | 38.9 | 45.5 | 40.6 | 13.2 |
| e3 | 9 | 9 | 50.0 | 46 | 27.5 | 26 |
| e3 | 7 | 3 | 30.0 | 76.4 | 16 | 7.2 |
| e3 | 12 | 10 | 45.5 | 49.1 | 15.8 | 34.2 |
| e3 | 12 | 2 | 14.3 | 70 | 26.1 | 3.3 |
| e3 | 14 | 4 | 22.2 | 60.2 | 30.2 | 8.8 |
| e3 | 7 | 3 | 30.0 | 78.8 | 17.3 | 3.6 |
| e3 | 14 | 4 | 22.2 | 71 | 20.3 | 8.1 |
| e3 | 12 | 1 | 7.7 | 71.8 | 25.5 | 2.2 |
| e6 | 9 | 4 | 30.8 | 82.7 | 12.1 | 4.7 |
| e6 | 7 | 4 | 36.4 | 62.6 | 17.3 | 19.6 |
| e6 | 10 | 4 | 28.6 | 77 | 12 | 10.4 |
| e6 | 7 | 3 | 30.0 | 74.2 | 18 | 7.4 |
| e6 | 7 | 3 | 30.0 | 79.8 | 8 | 11.7 |
| e6 | 11 | 3 | 21.4 | 67.4 | 20.2 | 11.9 |
| e6 | 8 | 3 | 27.3 | 74.5 | 19.5 | 5.5 |
| e6 | 9 | 2 | 18.2 | 70 | 23.2 | 6.4 |
| e6 | 13 | 6 | 31.6 | 57.8 | 25.1 | 16.4 |
| e6 | 12 | 3 | 20.0 | 54.6 | 29.8 | 15.1 |

Raw data of Experiment 2

This experiment evaluated the effects of the *Echinacea* in the conditioned fear test. We tested the effects of 1.5 mg/kg, as this dose showed the strongest effects in the elevated plus-maze.

As shown in above, we evaluated the behavior of rats during the application of the stressor, to see whether drug treatment changed the immediate responses to shock. The behavior of rats was checked again 24 h later to see whether the treatment affected the delayed behavioral deficits induced by shocks. To assess the effects of shocks in general, an unshocked control group was also included in this latter analysis.

Behavior During the Application of Electric Shocks

Legend: EXP, exploration; FRE, freezing; RES, resting; JUM, escape jumps (only frequency given); fr, frequency; t %, % of total time, shocked, vehicle, rats treated with vehicle and exposed to shocks; shocked, e1.5, rats treated with 1.5 mg/kg *Echinacea* extract and exposed to shocks.

| Group | EXPfr | FREfr | RESfr | JUMfr | EXPt % | FREt % | RESt % |
|---|---|---|---|---|---|---|---|
| shocked, vehicle | 24 | 13 | 22 | 1 | 62.5 | 16.3 | 17.5 |
| shocked, vehicle | 32 | 20 | 27 | 30 | 33.2 | 42.9 | 19.9 |
| shocked, vehicle | 33 | 24 | 26 | 17 | 50.9 | 32.2 | 12.7 |
| shocked, vehicle | 20 | 19 | 27 | 4 | 30.3 | 28.6 | 37.7 |
| shocked, vehicle | 24 | 12 | 21 | 13 | 41.4 | 32 | 22.8 |
| shocked, vehicle | 17 | 18 | 25 | 6 | 22.9 | 47.1 | 27 |
| shocked, vehicle | 11 | 19 | 20 | 1 | 15.4 | 56.8 | 24.3 |
| shocked, e1.5 | 22 | 27 | 25 | 10 | 23.9 | 44.3 | 25 |
| shocked, e1.5 | 38 | 21 | 32 | 48 | 51 | 23.5 | 21.5 |
| shocked, e1.5 | 33 | 15 | 18 | 14 | 60.1 | 17.4 | 17.3 |
| shocked, e1.5 | 47 | 11 | 27 | 46 | 55.9 | 17.6 | 22.2 |
| shocked, e1.5 | 25 | 18 | 20 | 10 | 38 | 38 | 18.2 |
| shocked, e1.5 | 26 | 10 | 19 | 7 | 61.8 | 9.8 | 24.6 |
| shocked, e1.5 | 20 | 15 | 24 | 25 | 41.6 | 24.1 | 30 |

Behavior One Day after the Stocks (Re-Exposure to the Environment Previously Associated with Shocks)

Legend: GRO, grooming; EXP, exploration; FRE, freezing; RES, resting; JUM, escape jumps (only frequency given); fr, frequency; t %, % of total time; Uc, unshocked control; Sv, the group treated with vehicle and shocked; Se1.5, the group treated with 1.5 mg/kg *Echinacea* extract and shocked.

| Group | GROfr | EXPfr | FREfr | RESfr | JUMfr | GROt % | EXPt % | FREt % | RESt % |
|---|---|---|---|---|---|---|---|---|---|
| Uc | 1 | 11 | 6 | 9 | 0 | 5 | 79.2 | 10 | 4.7 |
| Uc | 7 | 18 | 7 | 10 | 0 | 4 | 83.5 | 5.7 | 6 |
| Uc | 2 | 21 | 6 | 23 | 0 | 2 | 72.5 | 8.4 | 16.1 |
| Uc | 1 | 4 | 0 | 2 | 0 | 1.9 | 97.5 | 0 | 0.4 |
| Uc | 0 | 21 | 17 | 14 | 0 | 0 | 74.4 | 16.5 | 8.3 |
| Uc | 0 | 9 | 5 | 8 | 0 | 0 | 94.6 | 2.2 | 2.7 |
| Sv | 0 | 9 | 11 | 10 | 1 | 0 | 11 | 82 | 6.3 |
| Sv | 0 | 5 | 11 | 9 | 1 | 0 | 17.7 | 74.9 | 6.9 |
| Sv | 0 | 13 | 9 | 13 | 8 | 0 | 15.4 | 72.5 | 11.4 |
| Sv | 0 | 9 | 10 | 14 | 2 | 0 | 21.1 | 69.1 | 9.3 |
| Sv | 0 | 13 | 12 | 17 | 6 | 0 | 17.4 | 72.2 | 9.7 |
| Sv | 0 | 6 | 14 | 13 | 2 | 0 | 11.9 | 76.5 | 11 |
| Sv | 0 | 8 | 19 | 21 | 1 | 0 | 11.5 | 53.3 | 34.5 |
| Se1.5 | 0 | 25 | 11 | 12 | 25 | 0 | 23.2 | 67.3 | 8.6 |
| Se1.5 | 0 | 8 | 18 | 21 | 5 | 0 | 15.1 | 62.7 | 21.2 |
| Se1.5 | 0 | 31 | 17 | 26 | 22 | 0 | 24 | 40.4 | 34.4 |
| Se1.5 | 0 | 11 | 16 | 20 | 6 | 0 | 21.5 | 64.5 | 13.1 |
| Se1.5 | 0 | 8 | 12 | 13 | 0 | 0 | 29 | 45 | 25.3 |

-continued

| Group | GROfr | EXPfr | FREfr | RESfr | JUMfr | GROt % | EXPt % | FREt % | RESt % |
|---|---|---|---|---|---|---|---|---|---|
| Se1.5 | 0 | 52 | 31 | 27 | 53 | 0 | 29.4 | 52.8 | 16 |
| Se1.5 | 0 | 8 | 16 | 18 | 0 | 0 | 14.1 | 68 | 17.2 |

Raw data of Experiment 3

This experiment evaluated the effects of the *Echinacea* in the social interaction test of anxiety. We tested the effects of 1.5 mg/kg, as this dose showed the strongest effects in the elevated plus-maze.

Legend: RES, resting; EXP, exploration; SOC, social interactions; GRO, grooming; OFF, offense; DEF, defense; SUB, submissive posture; DOM, dominant posture; AGO, agonistic interactions (OFF+DEF+SUB+DOM); v, the group treated with vehicle; e1.5, the group treated with 1.5 mg/g *Echinacea* extract. Data show the duration of behaviors expressed as % of total time.

| Group | RES | EXP | SOC | GRO | OFF | DEF | SUB | DOM | AGO |
|---|---|---|---|---|---|---|---|---|---|
| v | 0 | 85.4 | 7.5 | 2.6 | 0 | 0 | 0 | 0 | 0 |
| v | 0 | 92.7 | 4.7 | 0.5 | 0 | 0 | 0 | 0 | 0 |
| v | 0.4 | 90.9 | 5.9 | 0.4 | 1 | 0.2 | 0.2 | 0 | 1.4 |
| v | 0.3 | 91.7 | 3.1 | 0.4 | 0.4 | 0.5 | 0 | 0 | 0.9 |
| v | 0 | 94.9 | 4.4 | 0.3 | 0 | 0 | 0 | 0 | 0 |
| v | 0 | 84.1 | 7 | 8.3 | 0 | 0 | 0 | 0 | 0 |
| v | 0 | 91.3 | 7.9 | 0 | 0 | 0 | 0 | 0 | 0 |
| v | 0 | 91.1 | 6 | 0 | 0 | 0 | 0 | 0 | 0 |
| v | 0 | 86 | 9.1 | 0 | 0 | 0 | 0 | 0 | 0 |
| v | 1.9 | 85.9 | 3.4 | 3 | 0 | 0 | 0 | 0 | 0 |
| e1.5 | 0 | 93 | 4.6 | 0.2 | 0 | 0 | 0 | 0 | 0 |
| e1.5 | 0 | 86 | 6.1 | 2.4 | 0 | 0 | 0 | 0 | 0 |
| e1.5 | 0 | 82.9 | 8.4 | 6.1 | 0 | 0 | 0 | 0 | 0 |
| e1.5 | 0 | 94.2 | 4.1 | 1.3 | 0 | 0 | 0 | 0 | 0 |
| e1.5 | 0 | 87.5 | 9.5 | 0 | 0.5 | 0 | 0 | 0 | 0.5 |
| e1.5 | 0.2 | 83 | 15.3 | 0 | 0.1 | 0.2 | 0 | 0 | 0.3 |
| e1.5 | 0 | 88.2 | 10.3 | 0.5 | 0.1 | 0.1 | 0 | 0 | 0.2 |
| e1.5 | 0 | 86.2 | 12.1 | 0.2 | 0.1 | 0 | 0 | 0 | 0.1 |
| e1.5 | 0 | 81.9 | 13.6 | 0.1 | 1.8 | 0.4 | 0 | 0 | 2.2 |
| e1.5 | 0 | 86 | 7.3 | 0.4 | 0.3 | 1.1 | 0 | 0 | 1.4 |

Raw Data of the Preliminary Human Study

| Subject code | B1 | B2 | T1 | T3 | T7 | FU7 | FU14 |
|---|---|---|---|---|---|---|---|
| | | | State anxiety | | | | |
| #1 | 41 | 44 | 51 | 41 | | | |
| #2 | 44 | 65 | 51 | 40 | | | |
| #3 | 52 | 55 | 44 | 38 | | | |
| #4 | 50 | 54 | 49 | 50 | 48 | 47 | 48 |
| #5 | 54 | 52 | 47 | 48 | 39 | 37 | 37 |
| #6 | 56 | 55 | 43 | 46 | 41 | 40 | 41 |
| #7 * | 51 | 46 | 38 | 37 | 35 | 36 | 41 |
| | | | Trait anxiety | | | | |
| #1 | 45 | 42 | 43 | 41 | | | |
| #2 | 42 | 59 | n.a. | n.a. | | | |
| #3 | 62 | 63 | 52 | 41 | | | |
| #4 | 58 | 56 | 50 | 47 | 43 | 44 | 42 |
| #5 | 50 | 41 | 41 | 42 | 40 | 40 | 36 |
| #6 | 55 | 52 | 48 | 43 | 35 | 36 | 36 |
| #7 * | 55 | 66 | 63 | 62 | 53 | 62 | 52 |

Legend. B1, baseline 1 (recorded approximately 6 days before treatment; B2, baseline 2 (recorded approximately 3 days before treatment; T1, anxiety score 1.5-2 h after the first treatment; T3, anxiety score on the third day of treatment; T7, anxiety score on the 7th day of treatment; FU7, follow-up (anxiety score 7 days after treatment cessation); FU14, follow-up (anxiety score 14 days after treatment cessation); n.a., the subject failed to fill in the second page of the inventory; *, the subject took half of the dose (one treatment in the morning). All the other subjects received two treatments (in the morning and in the evening).

Statistical Evaluation of Experiment 1A

This experiment evaluated the effects of 0 (vehicle), 0.5, 1, and 2 mg dry residue of *Echinacea* per kg body weight in Wistar rats.

Legend: vehicle, rats treated with vehicle; e05, rats treated with 0.5 mg/kg *Echinacea* extract; e1, rats treated with 1 mg/kg *Echinacea* extract; e2, rats treated with 2 mg/kg *Echinacea* extract; CLe, closed arm entries (measure of locomotor behavior); OPe, open arm entries (measure of anxiety); % OPe, % open arm entries (open arm entries*100/total arm entries; measure of anxiety); CL % t, time spent in closed arms (expressed as % of total time); CE % t, time spent in the central arena (expressed as % of total time); OP % t, time spent in open arms (expressed as % of total time); SEM, standard error of the mean; H(3, 40), the coefficient of Kruskal-Wallis ANOVA analysis; p, statistical likelihood of not having statistically significant differences between groups. Sample size was 10 per group.

The values printed in bold were statistically significantly different from the vehicle group ($p < 0.01$ at least).

| Group | CLe | SEM | OPe | SEM | % OPe | SEM | CL % t | SEM | CE % t | SEM | OP % t | SEM |
|---|---|---|---|---|---|---|---|---|---|---|---|---|
| vehicle | 6.60 | 0.83 | 2.80 | 0.65 | 28.71 | 2.66 | 78.51 | 2.19 | 12.32 | 2.23 | 8.76 | 1.19 |
| e05 | 7.30 | 0.63 | 3.80 | 0.61 | 32.59 | 3.26 | 75.01 | 3.05 | 12.40 | 1.91 | 12.17 | 1.78 |
| e1 | 8.80 | 1.16 | 3.60 | 0.73 | 27.17 | 2.21 | 69.13 | 6.36 | 18.00 | 4.10 | 12.42 | 2.33 |
| e2 | 8.30 | 0.91 | 4.30 | 0.56 | 33.33 | 3.14 | 65.68 | 4.18 | 16.74 | 2.70 | 17.09 | 1.99 |
| H(3, 40) | 2.69 | | 3.51 | | 2.53 | | 6.25 | | 3.18 | | 8.59 | |
| p< | 0.4 | | 0.3 | | 0.5 | | 0.099 | | 0.4 | | 0.035 | |

Statistical Evaluation of Experiment 1B

This experiment evaluated the effects of 0 (vehicle), 1.5, 3, and 6 mg dry residue of *Echinacea* per kg body weight in Wistar rats.

Legend: vehicle, rats treated with vehicle; e1.5, rats treated with 1.5 mg/kg *Echinacea* extract; e3, rats treated with 3 mg/kg *Echinacea* extract; e6, rats treated with 6 mg/kg *Echinacea* extract; CLe, closed arm entries (measure of locomotor behavior); OPe, open arm entries (measure of anxiety); % OPe % open arm entries (open arm entries*100/total arm entries; measure of anxiety); CL % t, time spent in closed arms (expressed as % of total time); CE % t, time spent in the central arena (expressed as % of total time); OP % t, time spent in open arms (expressed as % of total time); SEM, standard error of the mean; H(3, 39), the coefficient of Kruskal-Wallis ANOVA analysis; p, statistical likelihood of not having statistically significant differences between groups. Sample size was 9-10 per group.

The values printed in bold were statistically significantly different from the vehicle group ($p<0.03$ at least).

| Group | CLe | SEM | OPe | SEM | % OPe | SEM | CL % t | SEM | CE % t | SEM | OP % t | SEM |
|---|---|---|---|---|---|---|---|---|---|---|---|---|
| vehicle | 8.20 | 0.87 | 3.50 | 0.79 | 27.65 | 3.24 | 68.91 | 4.34 | 20.32 | 3.66 | 10.30 | 2.68 |
| e1.5 | 8.67 | 0.53 | 5.33 | 0.55 | 37.60 | 2.08 | 55.21 | 3.86 | 22.84 | 2.14 | 21.41 | 4.30 |
| e3 | 10.80 | 0.80 | 5.00 | 0.97 | 30.19 | 4.36 | 62.21 | 4.09 | 24.96 | 2.48 | 12.23 | 3.32 |
| e6 | 9.30 | 0.68 | 3.50 | 0.34 | 27.42 | 1.82 | 70.06 | 2.97 | 18.52 | 2.09 | 10.91 | 1.58 |
| H(3, 39) | 5.53 | | 7.14 | | 8.45 | | 7.63 | | 4.60 | | 8.16 | |
| p | 0.13 | | 0.067 | | 0.037 | | 0.054 | | 0.20 | | 0.042 | |

Statistical Evaluation of Experiment 2

This experiment evaluated the effects of the *Echinacea* in the conditioned fear test. We tested the effects of 1.5 mg/kg, as this dose showed the strongest effects in the elevated plus-maze. *Echinacea* treatment did not affect behavior during shocks but ameliorated the delayed behavioral deficit induced by shock exposure Behavior During Shock Exposure Legend: LX, exploration; FR, freezing; RE, resting; JU, escape jumps (only frequency given); fr, frequency; t%, % of total time, Sv, rats treated with vehicle and exposed to shocks; Se1.5, rats treated with 1.5 mg/kg *Echinacea* extract and exposed to shocks; SEM, standard error of the mean; H(1, 14), the coefficient of Kruskal-Wallis ANOVA analysis; p, statistical likelihood of not having statistically significant differences between groups. Sample size was 7 per group.

| Group | EXfr | SEM | FRfr | SEM | REfr | SEM | JUfr | SEM | EXt % | SEM | FRt % | SEM | REt % | SEM |
|---|---|---|---|---|---|---|---|---|---|---|---|---|---|---|
| Sv | 23.00 | 2.98 | 17.86 | 1.56 | 24.00 | 1.11 | 10.29 | 4.00 | 36.66 | 6.15 | 36.56 | 5.06 | 23.13 | 3.01 |
| Se1.5 | 30.14 | 3.67 | 16.71 | 2.23 | 23.57 | 1.89 | 22.86 | 6.61 | 47.47 | 5.18 | 24.96 | 4.60 | 22.69 | 1.64 |
| H(1, 14) | 2.17 | | 0.41 | | 0.33 | | 2.56 | | 1.8 | | 2.15 | | 0.01 | |
| p | 0.14 | | 0.5 | | 0.6 | | 0.11 | | 0.17 | | 0.14 | | 0.9 | |

Behavior One Day after the Shocks (Re-Exposure to the Environment Previously Associated with Shocks)

Legend: GRO, grooming; EXP, exploration; FRE, freezing; REX resting; JUM, escape jumps (only frequency given); fr, frequency; t %, % of total time; Uc, unshocked control; Sv, the group treated with vehicle and shocked; Se1.5, rats treated with 1.5 mg/kg *Echinacea* extract and shocked; SEM, standard error of the mean; H(1, 21), the coefficient of Kruskal-Wallis ANOVA analysis; p, statistical likelihood of not having statistically significant differences between groups. Values printed in bold differ significantly from those obtained in unshocked controls. Underlined values in the *Echinacea* treated group differ significantly from those obtained in shocked, vehicle-treated rats. Sample size was 7 per group.

| Group | GROfr ± SEM | EXPfr ± SEM | FREfr ± SEM | RESfr ± SEM | JUMfr ± SEM | GROi % ± SEM | EXPt % ± SEM | FREt % ± SEM | RESi % ± SEM |
|---|---|---|---|---|---|---|---|---|---|
| Uc | 1.83 ± 1.08 | 14.00 ± 2.88 | 6.83 ± 2.27 | 11.00 ± 2.88 | 0.00 ± 0.00 | 2.15 ± 0.83 | 83.62 ± 4.25 | 7.13 ± 2.41 | 6.37 ± 2.24 |
| Sv | 0.00 ± 0.00 | 9.00 ± 1.18 | 12.29 ± 1.27 | 13.86 ± 1.55 | 3.00 ± 1.07 | 0.00 ± 0.00 | 15.14 ± 1.45 | 71.50 ± 3.40 | 12.73 ± 3.70 |
| Se1.5 | 0.00 ± 0.00 | 20.43 ± 6.33 | 17.29 ± 2.49 | 19.57 ± 2.19 | 15.86 ± 7.27 | 0.00 ± 0.00 | 22.33 ± 2.28 | 57.24 ± 4.23 | 19.40 ± 3.22 |
| H(2, N = 21) | 10.92 | 2.09 | 8.57 | 5.33 | 9.59 | 10.91 | 14.22 | 15.43 | 8.62 |
| p | 0.004 | 0.4 | 0.013 | 0.069 | 0.008 | 0.004 | 0.001 | 0.0004 | 0.013 |

Statistical Evaluation of Experiment 3

This experiment evaluated the effects of the *Echinacea* in the social interaction test of anxiety. We tested the effects of 1.5 mg/kg, as this dose showed the strongest effects in the elevated plus-maze.

Legend: RES, resting; EXP, exploration; SOC, social interactions; GRO, grooming; OFF, offense; DEE, defense; SUB, submissive posture; DOM, dominant posture; AGO, agonistic interactions (OFF+DEF+SUB+DOM); vehicle, the group treated with vehicle; e1.5, the group treated with 1.5 mg/kg *Echinacea* extract; SEM, standard error of the mean; H(1, 21), the coefficient of Kruskal-Wallis ANOVA analysis; p, statistical likelihood of not having statistically significant differences between groups. Data show the duration of behaviors expressed as % of total time. Data printed in bold differ significantly from vehicle controls. Sample size was 10 per group.

The seven days of treatment and the follow-up was completed by 4 subjects, one of which misunderstood the dose (see above). Therefore, sample size was 3 for this study. The evolution of state anxiety scores was as follows: 53.6±1.0 (baseline). 46.4±1.8 (1.5-2 h after the first treatment), 48.1±1.3 (three days of treatment), 42.7±2.7 (one week of treatment). 41.3±2.9 (one week after treatment cessation), and 42.0±3.2 (two weeks after treatment cessation). The evolution of trait anxiety scores was as follows: 52.0±3.4 (baseline), 46.5±2.8 (1.5-2 h after the first treatment), 43.9±1.5 (three days of treatment), 39.4±2.4 (one week of treatment), 40.1±2.4 (one week after treatment cessation), and 38.0±2.0 (two weeks after treatment cessation). The level of state and trait anxiety was similar (Ftype(1,4)=0.8; p<0.4), but treatment decreased anxiety scores significantly (Ftreatment(5, 20)=18.07; p<0.0001). There was no interaction between factors (Finteraction(5,20)=0.56; p<0.7). Post-hoc analyses

| Group | RES ± SEM | EXP ± SEM | SOC ± SEM | GRO ± SEM | OFF ± SEM | DEF ± SEM | SUB ± SEM | AGO ± SEM |
|---|---|---|---|---|---|---|---|---|
| vehicle | 0.26 ± 0.19 | 89.40 ± 1.17 | 5.90 ± 0.63 | 1.55 ± 0.83 | 0.14 ± 0.10 | 0.07 ± 0.05 | 0.02 ± 0.02 | 0.23 ± 0.16 |
| e1.5 | 0.02 ± 0.02 | 86.89 ± 1.29 | 9.13 ± 1.19 | 1.12 ± 0.60 | 0.29 ± 0.18 | 0.18 ± 0.11 | 0.00 ± 0.00 | 0.47 ± 0.24 |
| H(1, 20) | 1.54 | 0.96 | 4.16 | 0.07 | 2.11 | 0.78 | 1.00 | 2.35 |
| p | 0.2 | 0.3 | 0.04 | 0.8 | 0.14 | 0.4 | 0.3 | 0.12 |

Statistical Evaluation of the Preliminary Human Study

This study evaluated the effects of the *Echinacea* extract in humans.

Values obtained in the two baseline tests were as follows. State and trait anxiety scores recorded at baseline 1 were 49.6±2.4, and 51.9±3.1, respectively. State and trait anxiety scores recorded at baseline 2 were 54.2±2.7, and 52.2±3.7, respectively. Differences were not significant (Fstate(1,10) =1.46; p>0.2; Ftrait(1,10) 0.1; p>0.9). Therefore, the average of baselines was considered in the following calculi.

The three-day treatment was completed by 7 subjects, out of which one misunderstood the dose. In addition, one subject failed to fill in the second page of the score sheet. Therefore, the sample size was 6 for state anxiety and 5 for trait anxiety. The evolution of state anxiety scores was as follows: 51.9±1.9 (baseline), 47.5±1.4 (1.5-2 h after the first treatment), and 43.9±2.0 (third day of treatment). The evolution of trait anxiety scores was as follows: 52.4±3.5 (baseline), 46.9±2.1 (1.5-2 h after the first treatment), and 42.8±1.1 (third day of treatment). Data were analyzed by two-factor ANOVA, where factor 1 was the type of anxiety (state vs. trait), whereas factor 2 was time (treatment). The level of state and trait anxiety was similar (Ftype(1,9)=0.1; p<0.9), but treatment decreased anxiety scores significantly (Ftreatment(2,18)=11.41; p<0.001). There was no interaction between factors (Finteraction(2,18)=0.1; p<0.9). Post-hoc analyses showed that anxiety was significantly reduced immediately after the first treatment (p<0.02), and the decrease was even more marked after three days of treatment (p<0.001). Note that the treatment reduced anxiety scores below 45, which is the threshold value for increased anxiety.

showed that anxiety was significantly reduced immediately after the first treatment (p<0.01), and the decrease was even more marked in the following days (p<0.001 at each time point). Note that the treatment reduced anxiety scores below 45, which is the threshold value for increased anxiety. Important note. No dropouts were noticed during treatments. The lack of complete records in 3 subjects was purely due to time constraints.

Results a) Experiment 1

Figure 2:
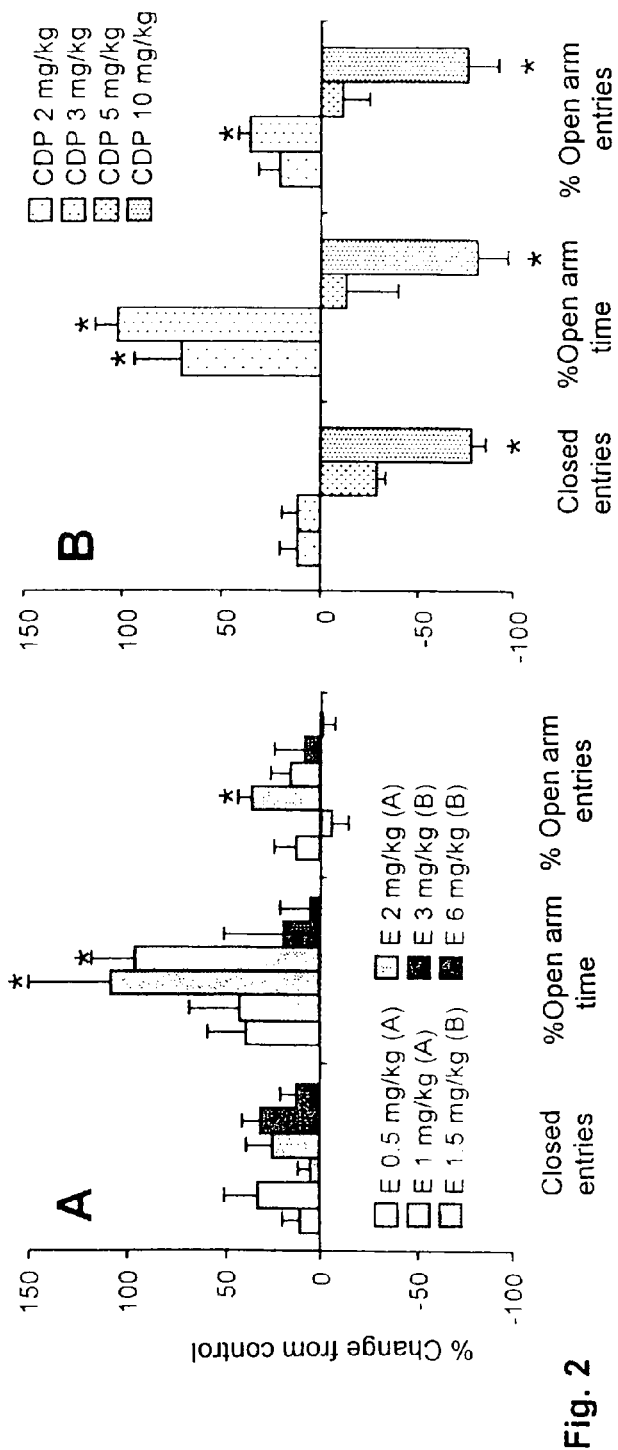
FIG. 2 shows the effect of the *Echinacea* extract (E; panel A) and chlordiazepoxide (CDP, panel B) on anxiety in the elevated plus-maze test of anxiety.

The main findings were reiterated in FIG. 2 (panel A). The results of Experiments 1A and 1B were presented together (the letters A and B placed in brackets after the *Echinacea* doses refer to the Experiment 1A and 1B, respectively). Data were shown as differences from control values obtained within each experiment. For comparison, FIG. 2 (panel B) shows the dose-response curve of the benzodiazepine chlordiazepoxide, as obtained in our laboratory.

As it can be seen from FIG. 2, the *Echinacea* extract reduced anxiety at doses comparable with those of chlordiazepoxide. As expected, chlordiazepoxide was highly sedative at higher doses.

Locomotor behavior (closed arm entries) was not affected by the extract in either concentration. Open arm exploration provided a bell-shaped dose response curve. The extract was surprisingly efficacious: it decreased anxiety already at 1.5 mg/kg. Thus, the efficacy of the extract was comparable with that of chlordiazepoxide. The loss of the effect occurred at similar doses with both the *Echinacea* extract and chlordiazepoxide. The *Echinacea* extract, however, did not suppress locomotion, whereas a significant locomotor suppression occurred with chlordiazepoxide. Noteworthy, this effect of benzodiazepines is well known.

b) Experiment 2

Shocks resulted in a significant increase in plasma glucocorticoids, but this was not affected by *Echinacea* (plasma glucocorticoid levels were 426.4±187.1, 784.5±158.7, and 736.0±128.3 nmol/l in unshocked controls, vehicle-treated, shocked controls, and *Echinacea*-treated, shocked rats, respectively). The immediate behavioral response to shocks was not affected by *Echinacea* (see above the statistical evaluation of Experiment 2).

The behavioral consequences of shock exposure were clearly visible on the next day. As compared with controls, shocked rats showed a dramatic increase in freezing, resting, and escape jumps, whereas exploration and grooming decreased markedly. These responses were significantly, although not dramatically reduced by *Echinacea* treatment (FIG. 3.).

As it can be seen from FIG. 3, that shocks dramatically reduced the duration of exploration (expressed as % time; EXPt %) and increased freezing (expressed as % time; FREt %). Pre-treatment with the *Echinacea* extract (shocked E1.5 mg/kg) slightly but significantly reduced this behavioral deficit as compared to rats pretreated with vehicle before shock exposure (shocked control).

Thus, the extract ameliorated the development of conditioned fear.

c) Experiment 3

Both resting and agonistic interactions were rare. Exploration was not affected (see above the statistical evaluation of Experiment 3).

As it can be seen from FIG. 4, the *Echinacea* extract significantly enhanced social interactions, demonstrating anxiolytic activity in this test as well.

d) The Preliminary Human Study

Figure 5:
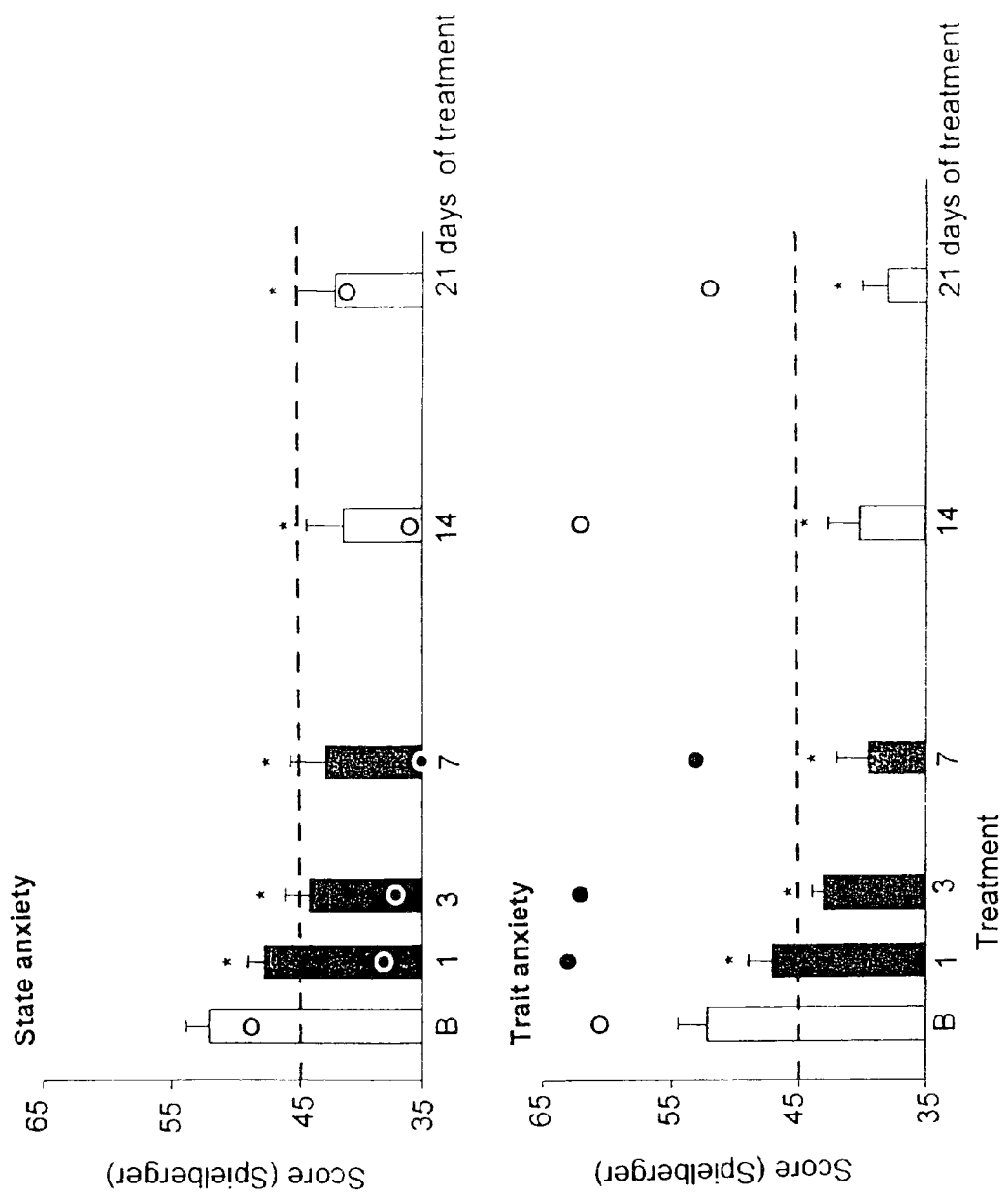
FIG. 5 shows an overview of the preliminary human study. Meanings of the signs: B: baseline (scores obtained several days before treatment); dark: scores obtained during treatment; light: scores obtained after the termination of treatment; horizontal bar: the duration of treatment; circles: data obtained in one subject that took half of the dose (due to a misunderstanding); dotted horizontal line, the threshold value for significant anxiety;
*: significantly different from baseline.

An overview of the findings was shown in FIG. 5. The 1 ml dose (7.5 mg dry residue) significantly reduced anxiety scores within 1.5-2 h. At this time point, anxiety scores were still higher than the threshold value for significant anxiety (score 45). The same dose reduced anxiety below score 45 within 3 days when administered twice daily (total dose per day: 2 ml, i.e. 15 mg). A mild further reduction was noticed after 7 days of treatment. The effect was persistent, as low anxiety scores were noticed 7 and 14 days after the cessation of treatment. A lower dose (1 ml, i.e. 7.5 mg per day) had beneficial effects on state anxiety, but less pronounced effects on trait anxiety. In the latter anxiety type, a reduction was noticed after 7 days of treatment but this mild effect was lost after the cessation of treatment.

Discussion of the Results

1. Efficacy

Hydro-alcoholic extracts of *Echinacea* have been reported to be administered in various ways, usually sub-chronically or chronically (from one week to several weeks). For testing its immunological and various other (infection-related) effects, the daily doses administered to laboratory rodents range from 30 mg/kg to 1 g (Currier and Miller 2000; Di Carlo et al., 2005; Goel et al., 2002; Rehman et al., 1999; Rusu et al., 2005). Compared to these doses (effective as immunostimulants or against infections), the anxiolytic effect was induced at surprisingly low doses (1.5 mg/kg). Thus, the extract was considerably more potent in anxiety tests than in laboratory tests related to its traditional uses. The extract even loosed its anxiolytic efficacy at higher doses, which main explain why this effect has not been noticed before. In the human study, 2 ml *Echinacea* extract (which is several times smaller than the dose used for traditional indications) rapidly and significantly reduced anxiety, and the effect persisted at least two weeks post-treatment.

The extracts showed surprisingly strong anxiolytic effects in the elevated plus-maze test, where the 1.5 mg/kg dose was fully effective in reducing anxiety. The dose-response curve of the extract was very similar with that of chlordiazepoxide, a benzodiazepine currently used in the treatment of anxiety disorders. The same low dose ameliorated conditioned fear, and reduced anxiety in the social interaction test. Unlike with benzodiazepines, no sedative effect was noticed in either of these tests.

In humans, the effects of *Echinacea* treatment were surprisingly strong as compared with the available anxiolytics. In the study by Laakmann et al. (1998) both the benzodiazepine lorazepam (3×1 mg; total daily dose: 3 mg) and the serotonergic anxiolytic buspirone (3×5 mg; total daily dose: 15 mg) decreased anxiety scores as assessed by the State-Trait Anxiety Inventory. However, significant effects over placebo were noted after one week with lorazepam and 3 weeks after buspirone. In addition, State-Trait anxiety scores lower than 45 were obtained after three weeks of lorazepam and 6 weeks of buspirone treatment. Similar findings were reported by Delle Chiaie et al., (1995), and Lemoine et al. (1996). In our experiment, such low scores were obtained with *Echinacea* extracts (2×7.5 mg; daily dose 15 mg) within 3 days. Despite limitations (low sample size, lack of placebo control) our data strongly suggest that the *Echinacea* extract—at doses considerably lower than those used for traditional indications—can rapidly and effectively decrease anxiety in humans.

The rapid effects of the *Echinacea* extract may be surprising. It is worth to note that such rapid effects are not unprecedented. Although 1-2 weeks of treatment is required for a fill effect, benzodiazepines also decrease anxiety within 1-7 hours (Beechey et al., 1981; Giudicelli et al., 1978; Wilhelm and Roth, 1997).

2. Tolerability

*Echinacea* extracts are well tolerated (Barnes et al., 2005; Huntley et al., 2005). Adverse reactions are rare; precautions should only be taken in patients with allergy or asthma. In a randomized, double-blind, placebo-controlled trial, where *Echinacea purpurea* root extracts were evaluated against upper respiratory tract infections, the number of reported adverse effects—although present—did not differ between placebo and *Echinacea* treatment (Taylor et al., 2003). As the *Echinacea* extract showed anxiolytic activity at very low doses, it is highly probable that its adverse effects—when used at low doses as an anxiolytic—would even be less noticeable than with traditional uses.

3. Indications

Based on the results of this study, hydro-alcoholic root extracts of *Echinacea* have a considerable potential for the alternative treatment of natural anxiety and anxiety disorders of various kinds.

REFERENCES

Arevalo C. et al., *Pharmacol Biochem Behav*, 2001; 70: 123-131.
Barnes J. et al., *J Pharm Pharmacol*, 2005; 57: 929-954.
Barrett B. *Phytomedicine*, 2003; 10: 66-86.
Bauer R. *Z Arztl Fortbild*, 1996; 90: 111-115.
Beck C H, Fibiger H C. *J Neurosci*, 1995; 25: 709-720.
Beechey A P et al., Anaesthesia. 1981; 36: 10-15.
Benton D. et al., *Neuropsychobiology*, 1995; 32: 98-105.

Berrendero F, Maldonado R. *Psychopharmacology,* 2002; 163: 111-117.
Borchers A T. et al., *Am J Clin Nutr,* 2000; 72: 339-347.
Brown J S. et al., *J Exp Psychol* 1951; 41: 317-328.
Carroll D. et al., *Psychopharmacology,* 2000; 150: 220-225.
Croxford J L. *CNS Drugs,* 2003; 17: 179-202.
Currier N L, Miller S C. *Exp Gerontol,* 2000; 35: 627-639.
Delle Chiaie R, et al. J Clin Psychopharmacol. 1995; 15: 12-19.
Di Carlo G. et al., *Phytomedicine,* 2005; 12: 644-647.
Fabre L F, McLendon D. *J Clin Pharmacol,* 1981; 21 Suppl: 377S-382S.
File S E, Hyde J R G. *Br J Pharmacol,* 1978; 62:19-24.
Fluttert M. et al., *Lab Anim,* 2000; 34: 372-378.
Genn R F. et al., *Pharmacol Biochem Behav,* 2004; 77: 567-573.
Giudicelli J F, et al. Br J Clin Pharmacol. 1978; 5: 65-69.
Giuliani D. et al., *Pharmacol Res,* 2000; 41: 47-53.
Goel V. et al., *J Nur Biochem,* 2002; 13: 487-492.
Griebel G. et al., *Biol Psychiatry,* 2005; 57: 261-267.
Guy A P, Gardner C R. *Neuropsychobiology,* 1985; 13:194-200.
Haller J, et al., *Eur J Neurosci,* 2002; 16: 1395-1398.
Haller J. et al., *Eur J Neurosci.* 2004a; 19: 1906-1912.
Haller J. et al., *Behav Pharmacol,* 2004b; 15: 299-304.
Hill M N, Gorzalka B B. *Eur J Pharmacol,* 2004; 499: 291-295.
Hogg S. et al., *Pharmacol Biochem Behav,* 1996; 54: 21-30.
Huntley A L. et al., *Drug Safety,* 2005; 28: 387-400.
Laakmann G, et al. Psychopharmacology 1998; 136: 357-366.
Lemoine P, Rouillon F, Pouget D. Encephale. 1996; 22: 461-467.
Linde K. et al., *Cochrane Database Syst Rev.* 2006; (1): CD000530.
Luo X B. et al., *J Chromatogr A,* 2003; 986: 73-81.
Maccarrone M. et al., *Eur J Neurosci,* 2002; 15: 1178-1186.
Marco E M. et al., *Behav Pharmacol,* 2004; 15: 21-27.
Marin S, et al., *Pharmacol Biochem Behav,* 2003; 74: 649-656.
Martin M. et al. *Psychopharmacology,* 2002; 159: 379-387.
Matsuda L A. et al., *J Comp Neurol,* 1993; 327: 535-550.
McLaughlin P J. et al., *Pharmacol Biochem Behav,* 2005-81: 78-88.
Melchart D. et al., *Arch Fam Med* 1998: 7: 541-545.
Mishima S. et al., *Biol Pharm Bull,* 2004; 27: 1004-1009.
Munro S. et al., *Nature* 1993, 365: 61-65.
Navarro M. et al., *Neuroreport,* 1997; 8: 491-496.
Pclilati F. et al., *Phytochem Anal,* 2005; 16: 77-85.
Pellow S, File S E. *Pharmacol Biochem Behav,* 1986; 24: 407-413.
Percival S S. *Biochem Pharmacol,* 2000; 60: 155-158.
Perczel Forintos D., Kiss, Zs., Ajtay Gy. (Ed.). Orsz. Pszich. Neur. Int. Budapest, 2005.
Perfect M M. et al., *Herpes,* 2005; 12: 38-41.
Piomelli D. *Nat. Rev. Neurosci,* 2003; 4: 873-884.
Raduner S. et al. *JBC* Papers in Press. (Mar. 17, 2006; Manuscript M601074200; Latest version is at http://www.jbc.org/cgi/doi/10.1074/jbc.M601074200).
Randolph R K. et al., *Exp Biol Med* (Maywood), 2003; 228: 1051-1056.
Razic S. et al., *J Pharm Biomed Anal,* 2003; 33:845-850.
Rehman J. et al., *Immunol Lett,* 1999; 68:391-395.
Rodgers R J. et al., *Behav Pharmacol,* 2005; 16: 405-413.
Rodgers R J. et al., *Eur J Neurosci.* 2003; 17: 1279-1286.
Rodriguez de Fonseca F. et al., *J Pharmacol Exp Ther,* 1996, 276: 56-64.
Rusu M A. et al., *Phytother Res,* 2005; 19:744-749.
Schulz H. et al., *Planto Med,* 2002; 68:926-929.
Sethi B B. et al., *Biol Psychiatry,* 1986; 21: 3-10.
Speroni E. et al. *J Ethnopharmacol.* 2002; 79: 265-272.
Spielberger C D, Theory and research on anxiety. In CD Spielberger (Ed.) *Anxiety and behavior.* New York, Academic Press, 1966.
Spielberger C D, et al., State-Trait Anxiety Inventory for Adults. Manual, test booklet and scoring key. Mind Garden, Inc. 1983.
Taylor J A. et al., *JAMA* 2003; 290: 2824-2830.
Thude S, Classen B. *Phytochemistry,* 2005; 66: 1026-1032.
Tunving K. *Pediatrician* 1987; 14: 83-91.
Uriguen L. et al., *Neuropharmacology,* 2004; 46: 966-973.
Valjent E. et al., *Br J Pharmacol,* 2002; 135: 564-578.
Wack M, Blaschek W. *Carbohydr Res.* 2006 Apr. 19; [Epub ahead of print] PMID: 16631147
Wilhelm F R, Roth W T. Behav Res Ther. 1997; 35: 831-841.
Woelkart K. et al., *Planta Med,* 2005; 71: 701-705.
Wu L. et al., *Phytochemistry,* 2004; 65: 2477-2484.
Zink T., Chaffin J. *Am Fam Physician,* 1998; 58: 1133-1140

The invention claimed is:

1. A method for the sedation-free treatment of anxiety in a human suffering from an anxiety disorder, said method comprising administering a preparation comprising an effective amount of an alcoholic extract obtained from *Echinacea* root to the human.

2. The method of claim 1 wherein the *Echinacea* is *Echinacea purpurea, Echinacea angustifolia, Echinacea paffida,* or a combination thereof.

3. The method of claim 1 wherein the preparation is administered orally.

4. The method of claim 1 wherein the preparation is part of a pharmaceutical composition.

5. The method of claim 4 wherein the alcoholic extract is provided as an ethanolic tincture having a dry residue content of 0.2 to 5% w/w.

6. The method of claim 1 wherein the preparation further comprises a vitamin mix comprising B1, B2, niacin, pantothenic acid, B6, biotin, folic acid, B12 or C vitamin, or a mineral mix comprising calcium, magnesium and zinc.

7. The method of claim 1 wherein the ethanolic extract is provided as an ethanolic tincture which has a dry residue content of 0.5 to 1.5% w/w, and wherein the *Echinacea* is *Echinacea purpurea, Echinacea angustifolia, Echinacea paffida,* or a combination thereof.

8. The method of claim 5, wherein 1 to 5 ml of the ethanolic tincture is administered per day.

* * * * *